US012774298B2

(12) United States Patent
Gravelle et al.

(10) Patent No.: US 12,774,298 B2
(45) Date of Patent: Oct. 27, 2026

(54) AMORPHOUS FORM OF 5-BROMOPYRIDIN-3-YL 3-DEOXY-3-[4-(3,4,5-TRIFLUOROPHENYL)-1H-1,2,3-TRIAZOL-1-YL]-1-THIO-ALPHA-D-GALACTOPYRANOSIDE

(71) Applicant: GALECTO BIOTECH AB, Copenhagen (DK)

(72) Inventors: Lise Gravelle, Copenhagen (DK); Peter Timmins, Cheshire (GB); Anders Pedersen, Copenhagen (DK)

(73) Assignee: GALECTO BIOTECH AB, Copenhagen (DK)

( * ) Notice: Subject to any disclaimer, the term of this patent is extended or adjusted under 35 U.S.C. 154(b) by 594 days.

(21) Appl. No.: 17/415,314

(22) PCT Filed: Dec. 18, 2019

(86) PCT No.: PCT/EP2019/085912

§ 371 (c)(1),
(2) Date: Jun. 17, 2021

(87) PCT Pub. No.: WO2020/127461

PCT Pub. Date: Jun. 25, 2020

(65) Prior Publication Data

US 2022/0064204 A1 Mar. 3, 2022

(30) Foreign Application Priority Data

Dec. 19, 2018 (EP) .................................... 18213993
Feb. 25, 2019 (EP) .................................... 19159222
Feb. 25, 2019 (EP) .................................... 19159227

(51) Int. Cl.
*A61K 9/00* (2006.01)
*A61K 9/10* (2006.01)
*A61K 9/20* (2006.01)
*A61K 9/48* (2006.01)
*C07H 19/056* (2006.01)

(52) U.S. Cl.
CPC ......... *C07H 19/056* (2013.01); *A61K 9/0053* (2013.01); *A61K 9/10* (2013.01); *A61K 9/20* (2013.01); *A61K 9/48* (2013.01); *C07B 2200/13* (2013.01)

(58) Field of Classification Search
CPC ..... A61K 9/10; A61K 31/7056; A61K 9/1676
See application file for complete search history.

(56) References Cited

U.S. PATENT DOCUMENTS 5,573,783 A * 11/1996 Desieno ............... A61K 9/1676 424/490
8,026,286 B2 * 9/2011 Curatolo ................. A61P 29/00 424/468

FOREIGN PATENT DOCUMENTS

WO WO-2013105092 A1 * 7/2013 ........... A61K 31/135
WO 2016/120403 A1 8/2016

OTHER PUBLICATIONS

Girard, Trends in Glycoscience and Glycotechnology vol. 30 No. 172 (Jan.-May 2018) pp. SE211-SE220. (Year: 2018).*
Maincent, Drug Delivery and Translational Research (2018) 8:1714-1725. (Year: 2018).*
International Search Report and Written Opinion issued on Feb. 25, 2020 in corresponding International Application No. PCT/EP2019/085912; 14 pages.
Guy Van Den Mooter, "The use of amorphous solid dispersions: A formulation strategy to overcome poor solubility and dissolution rate", Drug Discovery Today: Technologies, vol. 9, No. 2, Jun. 1, 2012, pp. e79-e85.
Tu Van Duong et al., "The role of the carrier in the formulation of pharmaceutical solid dispersions. Part II: amorphous carriers", Expert Opinion On Drug Delivery, Jun. 17, 2016, pp. 1-14.
Surikutchi Bhanu Teja et al., "Drug-excipient behavior in polymeric amorphous solid dispersions.", Journal of Excipients and Food Chemicals, International Pharmaceutical Excipients Council, vol. 4, No. 3, Sep. 1, 2013, pp. 70-94.
Nemanja Kolasinac et al., "Spray coating as a powerful technique in preparation of solid dispersions with enhanced desloratadine dissolution rate", Drug Development and Industrial Pharmacy, vol. 39, No. 7, Jul. 5, 2013, pp. 1020-1027.
Amrit Paudel et al., "Manufacturing of solid dispersions of poorly water soluble drugs by spray drying: Formulation and process considerations", International Journal of Pharmaceutics, vol. 453, No. 1, Jul. 20, 2012, pp. 253-284.

* cited by examiner

*Primary Examiner* — Layla D Berry
(74) *Attorney, Agent, or Firm* — Maier & Maier, PLLC

(57) ABSTRACT

A stabilized amorphous form of a compound of formula I as well as compositions for oral administration including the compound of formula I in a therapeutically effective amount. Also, methods for treatment of a disease or disorder in which therapeutically effective amount of a composition including a compound of formula I is administered to a subject in need thereof.

25 Claims, 5 Drawing Sheets

AMORPHOUS FORM OF 5-BROMOPYRIDIN-3-YL 3-DEOXY-3-[4-(3,4,5-TRIFLUOROPHENYL)-1H-1,2,3-TRIAZOL-1-YL]-1-THIO-ALPHA-D-GALACTOPYRANOSIDE

FIELD

The present invention relates to an amorphous form of a compound of formula I. The amorphous form of the compound of formula I can be stabilized with polymers when sprayed onto inert particles as well as when prepared as an amorphous solid dispersion.

BACKGROUND

The compound of formula I has been described in international patent application publication number WO2016120403 as a galectin 3 inhibitor useful for treating various disorders or diseases, as described therein. The compound of formula I is highly crystalline but has relatively low solubility making it difficult to prepare a suitable formulation for toxicology and clinical studies.

SUMMARY

The amorphous form approaches described in the present description enable the preparation of convenient dosage forms for the treatment of mammalian, such as human disease, not possible without the invention. Thus, all herein described diseases, disorders and/or conditions can be treated with the formulations of the present invention. Material characterization of the compound of formula I shows that it is highly crystalline by XRPD. A high melting point of 233.7° C. suggests that it forms a very stable crystal structure. Thermogravimetric analysis (TGA) data shows no indication of hydration and Dynamic vapor sorption (DVS) shows that the compound of formula I is not hygroscopic and shows no indication of hydrate formation.

Excipients to enhance the solubility of the compound of formula I were required, and several iterations of solution formulations were developed for toxicology studies as issues were found with limiting exposure and poor tolerability in earlier solution formulations.

Two different amorphous formulations, both containing amorphous compound of formula I, were found and investigated, that is 1) an amorphous spray dried dispersion (ASD) and 2) a structured drug composition prepared by spray coating/drug layering the amorphous compound of formula I onto inert microspheres.

One ASD formulation was found to be stable for 4 weeks at 25° C./60% RH and 40° C./75% RH. One drug layered formulation of the compound of formula I coated onto inert microspheres was achieved and was found to be stable for 12 months at 25° C./60% RH and 6 months at 40° C./75%.

In a broad aspect, the present invention relates to an amorphous form of a compound of formula I (I)

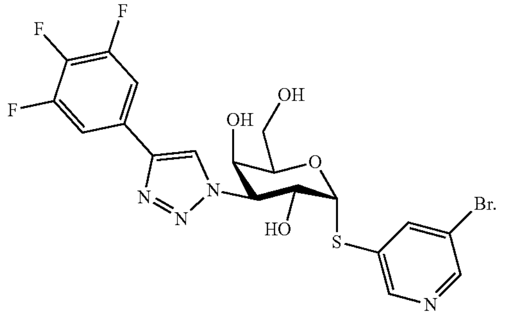

In another aspect, the present invention concerns a pharmaceutical composition comprising the amorphous form of the compound of formula I, and optionally a pharmaceutically acceptable additive.

In a further aspect, the present invention concerns a liquid composition comprising a mixture of a dissolved or dispersed polymer for stabilizing the amorphous form of the compound of formula I and a solution of a compound of formula I, and optionally a solution of a pharmaceutically acceptable additive.

In a still further aspect, the present invention relates to an amorphous solid dispersion composition comprising a mixture of an amorphous compound of formula I and a polymer for stabilizing the amorphous form of the compound of formula I, and optionally a pharmaceutically acceptable additive. In one embodiment the mixture comprises a weight ratio of the amorphous compound of formula I to the polymer in the range from 1:0.5 to 1:5, such as from 1:1 to 1:3, e.g. 1:2. In a further embodiment the amorphous compound of formula I is present in a concentration from 0.5% w/w to 90% w/w and the polymer is present in a concentration of at least 0.1% w/w, and optionally a pharmaceutically acceptable additive adding up to 100% w/w.

In a further aspect, the present invention relates to a tablet or capsule composition for oral administration comprising the amorphous solid dispersion composition of the present invention. Typically, the present invention relates to a tablet composition. In a particular embodiment the oral composition, such as a tablet or capsule, is administered once daily. In another embodiment the oral composition, such as a tablet or capsule, is administered twice daily.

In a still further aspect, the present invention relates to a drug layered composition comprising a) an inert solid core having an outer surface and b) a mixture of amorphous compound of formula I, a polymer for stabilizing the amorphous form of the compound of formula I and optionally a pharmaceutically acceptable additive, wherein the mixture is a layer on the outer surface of the inert solid core. Typically, the mixture is deposited on to the surface of the inert solid core by spraying a solution of the mixture in a suitable solvent. In another embodiment the mixture comprises a weight ratio of the amorphous compound of formula I to the polymer in the range from 1:0.5 to 1:5, such as from 1:1 to 1:3, e.g. 1:2. In a further embodiment the amorphous compound of formula I is present in a concentration from 0.5% w/w to 20% w/w, the polymer is present in a concentration from 1% w/w to 40% w/w, the inert solid core is present in a concentration of 40% w/w to 98.5% w/w, and optionally a pharmaceutically acceptable additive adding up to 100% w/w.

In a further aspect the present invention relates to a capsule composition for oral administration, such as once daily or twice daily, comprising the drug layered composition of the present invention. It was found that the drug layered composition of the present invention would readily be enclosed in a pharmaceutical hard shell capsule either manually or by suitable manufacturing equipment and will allow tailoring of the dose included in the capsule.

In the above aspects and embodiments, where the polymer for stabilizing the amorphous form of the compound of formula I is part of the composition, such polymer is selected from the group consisting of one or more polyethylene glycol (PEG), carboxymethylethylcellulose (CMEC), ethyl cellulose, hydroxyethylcellulose (HEC), methyl cellulose (MC), polyvinylpyrrolidone vinyl acetate (PVPVA), Polyvinylpyrrolidone (PVP), such as (PVP K30), crospovidone, hydroxy propyl methyl cellulose (Hypromellose), e.g. Hypromellose 603 (HPMC 603), Hypromellose 606 (HPMC 606), Hypromellose 615 (HPMC 615), Hypromellose phthalate-55 (HP-55), and Hypromellose acetate succinate-LF (HPMCAS-LF), Eudragit L100-55, poloxamer, and Gelucire 44/14, preferably a hydroxy propyl methyl cellulose, such as HPMC 603.

In a further embodiment the pharmaceutically acceptable additive is present. When a layer is applied in the drug layered composition of the present invention the additive may comprise a pore forming excipient. When the pore forming excipient is present it is typically present in a concentration up to 20% w/w in the layer. The pore forming excipients as used herein are known to the person skilled in the art and is in one embodiment selected from the group consisting of Calcium Dihydrogen Phosphate, Lactose, Hydroxypropyl cellulose and microcrystalline cellulose also including mixtures hereof.

In the above aspects and embodiments, where the inert solid core is part of the composition, the inert solid core is made of a material selected from the group consisting of sugars, such as starch and sucrose, and microcrystalline cellulose (MCC), preferably MCC.

In a further embodiment the inert solid core has a size in the range from 50 to 2000 μm, such as 100 to 1400 μm.

In a further aspect the present invention relates to a method of preparing a liquid composition comprising a mixture of a dissolved or dispersed polymer for stabilizing the amorphous form of the compound of formula I and a solution of a compound of formula I, and optionally a solution of a pharmaceutically acceptable additive, comprising the steps of:

a) preparing a solution or dispersion of the polymer and dissolving the compound of formula I in the solution or dispersion, and optionally dissolving a pharmaceutically acceptable additive in the solution or dispersion, thereby providing the liquid composition; or b) preparing a first solution or dispersion of the polymer and a second solution of the compound of formula I, and mixing the first and second solution, and optionally dissolving a pharmaceutically acceptable additive in the first or second solution or dispersion, or the mixture, thereby providing the liquid composition.

In a still further aspect the present invention relates to a method of preparing an amorphous solid dispersion composition comprising a mixture of the amorphous compound of formula I and a polymer for stabilizing the amorphous form of the compound of formula I, and optionally a pharmaceutically acceptable additive, comprising the steps of:

spray drying a liquid composition comprising a mixture of a dissolved or dispersed polymer for stabilizing the amorphous form of the compound of formula I and a solution of a compound of formula I, and optionally a solution of a pharmaceutically acceptable additive; and collecting the amorphous solid dispersion composition.

As used herein and throughout the description and claims 'a solid dispersion' means a dry composition, such as a dry powder.

In a further aspect the present invention relates to a method of preparing a drug layered composition comprising a) an inert solid core having an outer surface and b) a mixture of the amorphous compound of formula I, a polymer for stabilizing the amorphous form of the compound of formula I and optionally a pharmaceutically acceptable additive, wherein the mixture is applied as a layer on the outer surface of the inert solid core, comprising the steps of: spraying a liquid composition comprising a mixture of a dissolved or dispersed polymer for 10 stabilizing the amorphous form of the compound of formula I and a solution of a compound of formula I, and optionally a solution of a pharmaceutically acceptable additive, onto an inert solid core and collecting the drug layered composition. In one embodiment the spraying is spray-coating or fluid bed coating.

In a further aspect the present invention concerns an oral composition comprising a compound of formula I (I)

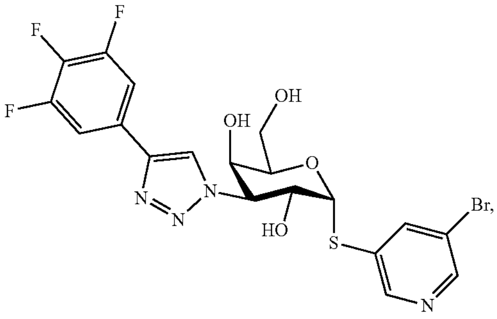

Br, and optionally a pharmaceutically acceptable additive, wherein the compound of formula I is present in an amount of 0.1 to 1000 mg, such as 1 to 1000 mg. Preferably, the composition is a solid oral composition, such as a tablet or capsule. Typically, one tablet or one capsule is one unit dosage form which then contains the amount of the compound of formula I. However, for treatment one or more unit dosages may be administered such as 1 to 4 unit dosages, for instance a capsule containing 5 mg of compound of formula I, or 4 capsules each containing 5 mg adding up to 20 mg dosage administered.

In an embodiment the oral composition is a unit dosage form.

In a further embodiment the compound of formula I is present in an amount of 5 to 900 mg, such as 10 to 800 mg, 20 to 700 mg, 30 to 600 mg, 40 to 500 mg, 50 to 400 mg, 60 to 300 mg, 70 to 200 mg, 80 to 100 mg. in another embodiment the compound of formula I is present in an amount of 0.1 mg to 1000 mg, such as 0.1 to 1 mg, e.g. 0.2 to 0.8 mg. One example is administration of 5 mg compound of formula I, another example is administration of 20 mg compound of formula I, a further example is administration of 50 mg of compound of formula I, and a still further example is administration of 200 mg of compound of formula I. Each unit dose may contain from 1 mg to 200 mg, for instance administration of 20 mg may be carried out by giving the human subjects 4 capsules each containing 5 mg compound of formula I.

In a still further embodiment, the pharmaceutically acceptable additive is present in a concentration from 0.1 to 99.5% w/w, such as 10% w/w to 99.5% w/w and the compound of formula I is present in a concentration from 0.5% w/w to 90% w/w.

In a further embodiment the pharmaceutically acceptable additive is one or more selected from the group consisting of polyethylene glycol (PEG), carboxymethylethylcellulose (CMEC), ethyl cellulose, hydroxyethylcellulose (HEC), methyl cellulose (MC), polyvinylpyrrolidone vinyl acetate (PVP/VA), Polyvinylpyrrolidone, hydroxy propyl methyl cellulose (Hypromellose), Hypromellose phthalate, Hypromellose acetate succinate, Eudragit, Gelucire 44/14, sugars, such as starch and sucrose, microcrystalline cellulose (MCC) and a pore forming excipient, such as Calcium Dihydrogen Phosphate, Lactose, Hydroxypropyl cellulose and microcrystalline cellulose as well as mixtures hereof.

In a further aspect the present invention relates to a composition of the present invention and any one of the above defined embodiments for use in a method for treatment of a disease or disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistance; obesity; Diastolic HF; asthma and other interstitial lung diseases, including Hermansky-Pudlak syndrome, mesothelioma; liver disorders, such as non-alcoholic steatohepatitis or non-alcoholic fatty liver disease, in a mammal, such as a human. In one embodiment the disease or disorder is NASH. In another embodiment the disease or disorder is a cancer. In a further embodiment the disease or disorder is kidney fibrosis. In an embodiment the oral composition is administered once daily, such as one to four unit dosages once daily. In another embodiment the oral composition is administered twice daily, such as one to four unit dosages twice daily. In particular, the once daily amount is from 5 mg to 900 mg. In another embodiment the once daily amount is from 0.1 to 5 mg, such as 0.1 to 1 mg. In particular, the twice daily amount is from 1 mg to 500 mg, such as 5 mg to 200 mg.

In a still further aspect the present invention relates to a method for treatment of a disease or disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistance; obesity; Diastolic HF; asthma and other interstitial lung diseases, including Hermansky-Pudlak syndrome, mesothelioma; liver disorders, such as non-alcoholic steatohepatitis or non-alcoholic fatty liver disease, in a mammal, comprising administering a therapeutically effective amount of the composition of the present invention, such as the amorphous solid dispersion composition or the drug layered composition, and any one of the above defined embodiments. In a further embodiment the oral composition is administered once daily or twice daily, such as one to four unit dosages once daily or twice daily. In particular, the once daily amount is from 5 mg to 900 mg. In particular, the twice daily amount is from 1 mg to 500 mg, such as 5 mg to 200 mg.

In an embodiment of the method for treatment the composition comprises the compound of formula I in an amount of 5 to 900 mg, such as 10-800 mg, 20-700 mg, 30 to 600 mg, 40 to 500 mg, 50 to 400 mg, 60 to 300 mg, 70 to 200 mg. In a further embodiment 1 to 4 unit dosages of compound of formula I is administered, such as 1 to 4 capsules or tablets each containing from 5 to 200 mg compound of formula I, such as 10 to 100 mg compound of formula I.

Another aspect of the present invention concerns combination therapy involving administering a compound of formula (I) of the present invention together with a therapeutically active compound different from the compound of formula (I) (interchangeable with "a different therapeutically active compound"). In one embodiment the present invention relates to a combination of a compound of formula (I) and a different therapeutically active compound for use in treatment of a disorder relating to the binding of a galectin-3 to a ligand in a mammal. Such disorders are disclosed below.

In an embodiment of the present invention, a therapeutically effective amount of at least one compound of formula (I) of the present invention is administered to a mammal in need thereof in combination with a different therapeutically active compound. In a further embodiment, said combination of a compound of formula (I) together with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; type 2 diabetes; insulin resistance; obesity; Diastolic HF; asthma and other interstitial lung diseases, including Hermansky-Pudlak syndrome, mesothelioma; liver disorders, such as non-alcoholic steatohepatitis or non-alcoholic fatty liver disease.

A non-limiting group of cancers given as examples of cancers that may be treated, managed and/or prevented by administration of a compound of formula (I) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (I) of the present invention and at least one additional therapeutic agent demonstrates therapeutic synergy. In some aspects of the methods of the present invention, a measurement of response to treatment observed after administering both at least one compound of formula (I) of the present invention and the additional therapeutic agent is improved over the same measurement of response to treatment observed after administering either the at least one compound of formula (I) of the present invention or the additional therapeutic agent alone.

A further aspect of the present invention concerns combination therapy involving administering a compound of formula (I) of the present invention together with an anti-fibrotic compound different form the compound of formula (I) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, PAT-1251 and PBI-4050.

A still further aspect of the present invention concerns combination therapy involving administering a compound of formula (I) in combination with a further conventional cancer treatment such as chemotherapy or radiotherapy, or treatment with immunostimulating substances, gene therapy, treatment with antibodies and treatment using dendritic cells, to a mammal in need thereof.

In an embodiment the compound of formula (I) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (I) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are known targets and some of these targets are described in Melero et al., Nature Reviews Cancer (2015). Examples of check point inhibitors administered together with the compound of formula (1) are Anti-PD-1: Nivolumab, Pembrolizumab, Cemiplimab. Anti-PD-L1: Atezolizumab, Avelumab, Durvalumab and one Anti-CTLA-4: Ipilimumab. Each one of these check point inhibitors can be made the subject of an embodiment in combination with any one of the compounds of formula (1).

In some embodiments of the present invention the compound of formula (I) is administered together with at least one additional therapeutic agent selected from an inhibitor of indoleamine-2,3-dioxygenase (IDO).

In some embodiments of the present invention the compound of formula (I) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (I) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

DETAILED DESCRIPTION

Figure 1:
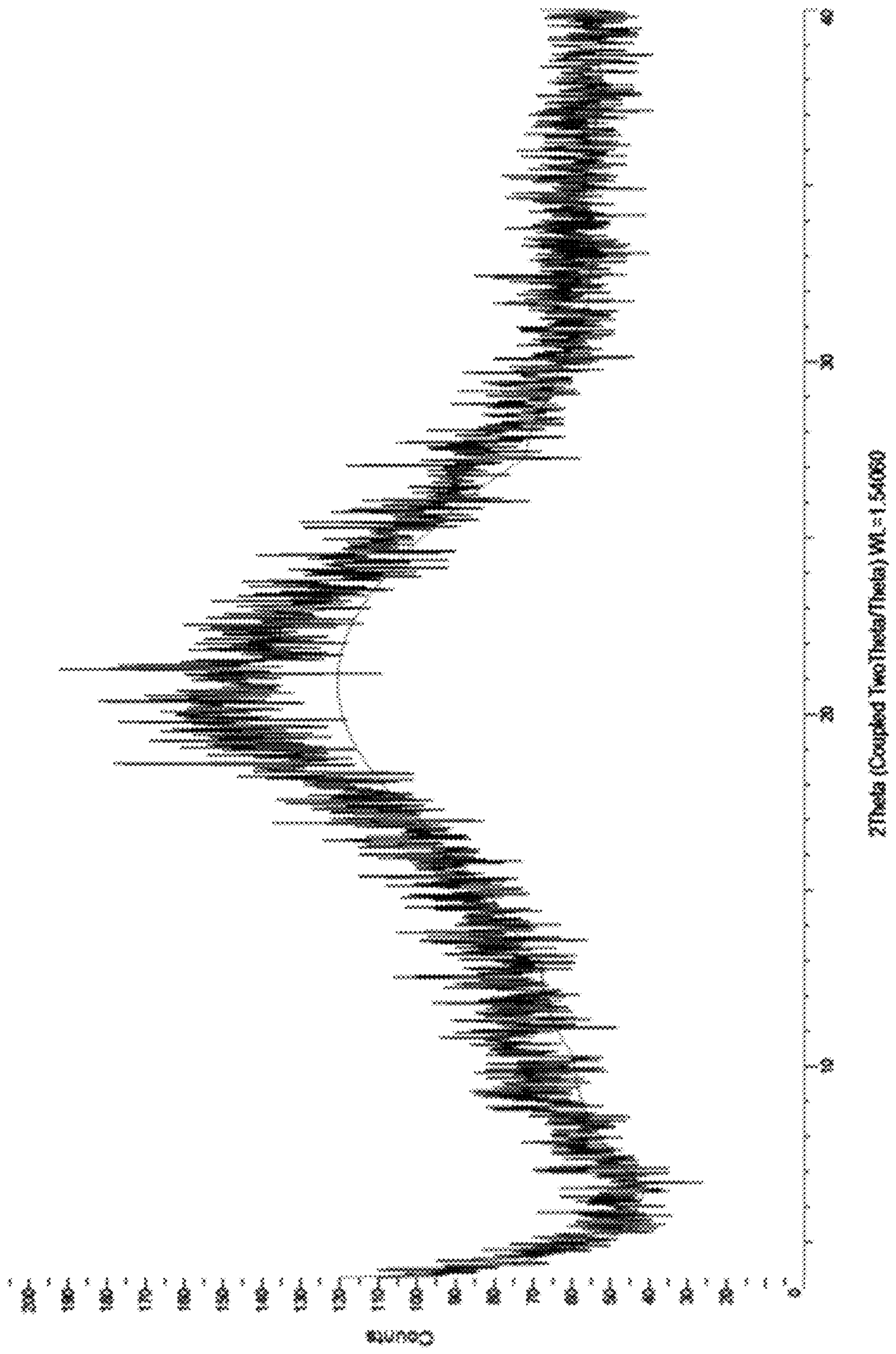
FIG. 1 shows an XRPD diffractogram of the API/HPMC 603 (1:2) SDD.

The compound of formula I is tested in a Phase 1, randomized, double-blind, placebo-controlled, first-in-human study in which the safety, tolerability, and pharmacokinetics of orally administered compound of formula I is evaluated in healthy adult subjects and adult subjects with indication of suspected Nonalcoholic steatohepatitis (NASH) and liver fibrosis.

This study aims to obtain safety, tolerability and pharmacokinetic data when the compound of formula I is administered orally as single doses and as multiple doses to healthy subjects. In addition, an optional part has been included to obtain safety and tolerability data when the compound of formula I is administered orally as multiple doses to subjects with suspected Nonalcoholic steatohepatitis (NASH) and liver fibrosis.

Based on results from a first in human study with single and multiple ascending doses it was concluded that the compound of formula (I) is both safe and well tolerated in man and favorable PK parameters support once daily or twice daily dosing for a specific dose range, typically from 5 mg to 200 mg once or twice daily, such as from 10 mg to 100 mg twice daily.

The compound of formula (I) has the chemical name (IUPAC) 5-Bromopyridin-3-yl 3-deoxy-3-[4-(3,4,5-trifluorophenyl)-1H-1,2,3-triazol-1-yl]-1-thio-a-D-galactopyranoside.

(I)

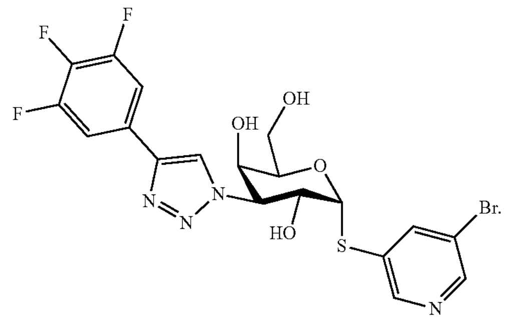

The compound is herein referred to as "the compound of formula I".

In the liquid composition comprising a mixture of a dissolved or dispersed polymer for stabilizing the amorphous form of the compound of formula I and a solution of a compound of formula I, the polymer is dissolved or dispersed in a suitable solvent which is dependent on the polymer used. The person skilled in the art can easily prepare a screening of various solvents as well as solvent mixtures to find the optimal solvent, for instance when HPMC is used dichloromethane, ethanol, water or a mixture of water and acetone are suitable. Furthermore, the compound of formula I can be dissolved in various solvents, such as acetone, tetrahydrofuran, DMSO, methanol, ethanol, dichloromethane, and here the skilled person can perform a screening of suitable solvents or solvent mixtures to find the optimal solvent. For instance, for the compound of formula I acetone and THF are preferred, and in particular a mixture of acetone in water is preferred. It should be noted that the polymer and compound of formula I may be dissolved in the same solvent.

When preparing the liquid composition comprising a mixture of a dissolved or dispersed polymer for stabilizing amorphous form of the compound of formula I and a solution of a compound of formula I, and optionally a solution of a pharmaceutically acceptable additive, the polymer is dissolved or dispersed in a first solvent and the compound of formula I is dissolved in a second solvent. The first and second solvent may be the same or different. For instance, the polymer may be dissolved in a solvent such as a mixture of acetone and water and the compound of formula I is then dissolved in the same solvent solution comprising the polymer. The order of dissolving the polymer and the compound of formula I is not critical, however, in one embodiment it is preferred to first dissolve the polymer and then the compound of formula I in the solvent comprising the polymer, and in a second embodiment it is preferred to dissolve the polymer in one solvent and the compound of formula I in a different solvent and the mix the two solutions. Optionally a pharmaceutically acceptable additive is dissolved in any one of the solutions, such as the first or second solution or dispersion, or in the mixture of the first and second solution or dispersion, or in the solution or dispersion comprising the polymer and/or the compound of formula I. The pharmaceutically acceptable additive is typically selected from suitable surfactants and/or pore forming excipients.

The amorphous compound of formula I can be stabilized as an amorphous solid dispersion or as a drug layered composition.

Thus, the present invention relates to an amorphous solid dispersion composition comprising a mixture of an amorphous compound of formula I and a polymer for stabilizing the amorphous form of the compound of formula I. Optionally a pharmaceutically acceptable additive may be comprised by the composition.

The weight ratio of the amorphous compound of formula I to the polymer can be modified dependent on the polymer employed to provide the most stable amorphous compound of formula I and a suitable range is from 1:0.5 to 1:5. To prevent recrystallization over time of the amorphous form of the compound of formula I in the amorphous solid dispersion a more preferred weight ratio is from 1:1 to 1:3, and it was found that the most optimal weight ratio is about 1:2. In addition, or independently, the amorphous compound of formula I is present in a concentration from 0.5% w/w to 90% w/w and the polymer is present in a concentration of at least 0.1% w/w, and optionally a pharmaceutically acceptable additive adding up to 100% w/w. For instance, the amorphous compound of formula I is present in a concentration selected from the range consisting of 1% w/w to 80% w/w, 2 to 70% w/w, 5 to 60% w/w, 10 to 50% w/w, and 20 to 40% w/w. Preferably, the amorphous compound of formula I is present in a concentration in the range from 30-40% w/w. For instance, the polymer is present in a concentration selected from the range consisting of 0.1% w/w to 99% w/w, 1 to 80% w/w, 5 to 70% w/w, 10 to 60% w/w, 20 to 50% w/w, and 30 to 40% w/w. Preferably, the polymer is present in a concentration in the range from 60-70% w/w.

The amorphous solid dispersion composition of the present invention can be filled into capsules or be compressed into tablets for oral administration.

Typically, the present invention relates to a tablet composition for oral administration comprising the amorphous solid dispersion composition of the present invention. The above-mentioned weight ratios of the amorphous compound of formula I to the polymer and concentrations of the amorphous compound of formula I and the polymer before adding excipients, such as binding agents, disintegrants, lubricants, bulking agents etc, also apply to the tablet of the present invention.

Further, the present invention relates to a drug layered composition comprising a) an inert solid core having an outer surface and b) a mixture of amorphous compound of formula I, a polymer for stabilizing the amorphous form of the compound of formula I, wherein the mixture is applied as a layer, for instance by spraying the mixture dissolved in a suitable solvent onto the outer surface of the inert solid core and evaporating off the solvent. The weight ratio of the amorphous compound of formula I to the polymer can be modified to provide the most stable drug layered composition and a suitable range is from 1:0.5 to 1:5. To prevent recrystallization over time of the amorphous form of the compound of formula I in the drug layered composition a more preferred weight ratio is from 1:1 to 1:3, and a most preferred weight ratio is about 1:2. In addition, or independently, the amorphous compound of formula I is present in a concentration from 0.5% w/w to 20% w/w, the polymer is present in a concentration from 1% w/w to 40% w/w, the inert solid core is present in a concentration of 40% w/w to 98.5% w/w, and optionally a pharmaceutically acceptable additive adding up to 100% w/w. For instance, the amorphous compound of formula I is present in a concentration selected from the range consisting of 1% w/w to 18% w/w, 5% w/w to 15% w/w, 7% w/w to 15% w/w, and 10% w/w to 14% w/w. For instance, the polymer is present in a concentration selected from the range consisting of 1% w/w to 40% w/w, 5% w/w to 35% w/w, 10% w/w to 30% w/w, and 15% w/w to 25% w/w. For instance, the inert solid core is present in a concentration selected from the range consisting of 45% w/w to 90% w/w, 50% w/w to 80% w/w, and 60% w/w to 70% w/w. Preferably, the drug layered composition comprises the amorphous compound of formula I in a concentration from 1-12% w/w, the polymer in a concentration from 2-24% w/w and the inert solid core in a concentration from 64-97% w/w. One example is 1.2% w/w amorphous compound of formula I, 2.4% w/w polymer and 96.4% w/w inert solid core and another example is 12% w/w amorphous compound of formula I, 24% w/w polymer and 64% w/w inert solid core. Another preferred embodiment concerns the drug layered composition comprising the amorphous compound of formula I in a concentration from 1-12% w/w, the polymer in a concentration from 2-24% w/w, the inert solid core in a concentration from 45-90% w/w and the pore forming excipient in a concentration from 5-20% w/w. One example is 12% w/w amorphous compound of formula I, 24% w/w polymer, 56.8% w/w inert solid core and 7.2% w/w pore forming excipient.

The mixture of amorphous compound of formula I and the polymer may be layered on the whole surface of the inert solid core, or just parts of the surface, since the inert solid core merely serves as a carrier.

The drug layered composition of the present invention is typically filled into a capsule suitable for oral administration. Such capsule may be a gelatin capsule, such as a size-0 Licap hard shell gelatin capsule.

In the above aspects and embodiments, where the polymer for stabilizing the amorphous form of the compound of formula I is part of the composition, such polymer is selected from the group consisting of one or more polyethylene glycol (PEG), carboxymethylethylcellulose (CMEC), ethyl cellulose, hydroxyethylcellulose (HEC), methyl cellulose (MC), polyvinylpyrrolidone vinyl acetate (PVPVA), Polyvinylpyrrolidone (PVP), hydroxy propyl methyl cellulose (Hypromellose or HPMC)), Hypromellose phthalate, and Hypromellose acetate succinate (HPMC-AS), Eudragit, poloxamer and Gelucire.

In preferred embodiments the polymer is selected from the group consisting of one or more polyethylene glycol (PEG300 to PEG10000), carboxymethylethylcellulose (CMEC), ethyl cellulose, hydroxyethylcellulose (HEC), methyl cellulose (MC), polyvinylpyrrolidone vinyl acetate (PVP/VA), Polyvinylpyrrolidone, such as (PVP K30), hydroxy propyl methyl cellulose (Hypromellose), e.g. Hypromellose 603 (HPMC 603), Hypromellose 606 (HPMC 606), Hypromellose 615 (HPMC 615), Hypromellose phthalate-55 (HP-55), and Hypromellose acetate succinate-LF (HPMCAS-LF), Eudragit L100-55, and Gelucire 44/14, preferably a hydroxy propyl methyl cellulose, such as HPMC 603.

In a further embodiment the amorphous compound of formula I is present in the composition, such as the drug layered composition or the amorphous solid dispersion composition, in an amount of 0.1 mg to 1000 mg, such as 5 mg to 900 mg. In a further embodiment the compound of formula I is present in an amount of 10-800 mg, 20-700 mg, 30 to 600 mg, 40 to 500 mg, 50 to 400 mg, 60 to 300 mg, 70 to 200 mg, 80 to 150 mg, or 90 to 100 mg. Preferably, one tablet contains the compound of formula I in an amount of 1-200 mg, such as from 5 to 100 mg. Preferably one capsule contains the compound of formula I in an amount of 1-200 mg, such as from 5 to 100 mg. In a typical embodiment this amount is administered once daily or twice daily.

In the above aspects and embodiments, where the inert solid core is part of the composition, the inert solid core is made of a material selected from the group consisting of sugars and microcrystalline cellulose (MCC).

Typically, the solid core is made of starch, sucrose, and microcrystalline cellulose (MCC), preferably MCC.

In a further embodiment the inert solid core has a size which is sufficiently large to carry the amorphous compound of formula I in a therapeutically relevant amount, and the size is typically at least 40 μm, such as at least 50 μm. Since the drug layered composition should fit into a capsule for oral administration the size should not exceed 3000 μm, such large particles may also carry less active drug and thus not be optimal for a capsule. Preferred inert cores should be in the range from 50 to 2000 μm, such as from 100 to 1400 μm, 100 to 200 μm, 200 to 355 μm, 355-500 μm, 500 to 710 μm, 710 to 1000 μm, and 1000 to 1400 μm.

In the method of preparing the amorphous solid dispersion composition of the present invention the spray drying of the liquid composition comprising the mixture of the dissolved or dispersed polymer for stabilizing amorphous form of the compound of formula I and a dissolved compound of formula I, can be performed using a ProCepT 4M8 Trix spray drier with the following parameters:

| | |
|---|---|
| Nozzle | 0.4-0.6 mm |
| Airspeed | 0.35 $m^3$/min |
| Nozzle air pressure | 30 PSI |
| Inlet temperature | 90° C. |
| Outlet temperature | 54.9° C. |
| Cyclone | Small |
| Sample feed rate | 1-3 mL/min |

In the method of preparing the drug layered composition of the present invention the spraying of the liquid composition comprising the mixture of the dissolved or dispersed polymer for stabilizing amorphous form of the compound of formula I and a dissolved compound of formula I, onto the inert solid core can be performed using a fluid bed fitted with a Wurster insert such as an Aeromatic STREA-1 or a Glatt GPCG3 with the following coating solution and parameters (wherein 'API' is used interchangeably with the 'compound of formula I'):

| | | |
|---|---|---|
| Composition of coating solution | Solvent | Acetone/water 80/20 |
| | Concentration of API | 3-30 mg/mL |
| | Concentration of HPMC603 | 6-60 mg/mL |
| Inlet Temperature | 45-60° C. | |
| Outlet Temperature | 30-45° C. | |
| Nozzle air pressure | 0.5-2.0 Bar | |
| Spray rate | 1-20 g/min | |
| Drying | 20-90 minutes at 50-80° C. (inlet temperature) | |

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may be performed in a chronic way. The patient to be treated may be a human subject diagnosed with pulmonary fibrosis or other types of lung fibrosis, kidney fibrosis or NASH.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (I) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. The combined amount of the active ingredient and of the pharmaceutically acceptable adjuvant, diluent, excipient and/or carrier may not constitute more than 100% by weight (100% w/w) of the composition, particularly the pharmaceutical composition.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

EXPERIMENTAL

Amorphous Solid Dispersion

A small trial batch of API-HPMC 603 (1:2) Spray Dried Dispersion (SDD) was prepared using a 4M8 TriX spray drier from ProCepT. One gram of HPMC 603 was dissolved in 22.2 mL of DCM/ethanol (1/1) solution (45 mg/mL) and 500 mg API was dissolved in 10 ml of tetrahydrofuran (THF) (50 mg/mL). The two solutions were mixed at room temperature, filtered through 45-μm filters followed by spray drying using the parameters listed below.

Parameters Used for Spray Drying:

| | |
|---|---|
| Nozzle | 0.4 mm |
| Airspeed | 0.35 $m^3$/min |
| Nozzle air pressure | 30 PSI |
| Inlet temperature | 90° C. |
| Outlet temperature | 54.9° C. |
| Cyclone | Small |
| Sample feed rate | 1 mL/min |

The prepared SDD was characterized by X-ray powder diffraction (XRPD) and modulated Differential Scanning calorimetry (mDSC). The XRPD data shows that the SDD was amorphous and a single Tg at 109° C. derived from the mDSC scan indicated the formation of a miscible system between API and HPMC 603 without phase separation. The yield of spray drying was 78% with an HPLC assay of 97%.

FIG. 1 is an XRPD diffractogram of the API/HPMC 603 (1:2) SDD.

Figure 2:
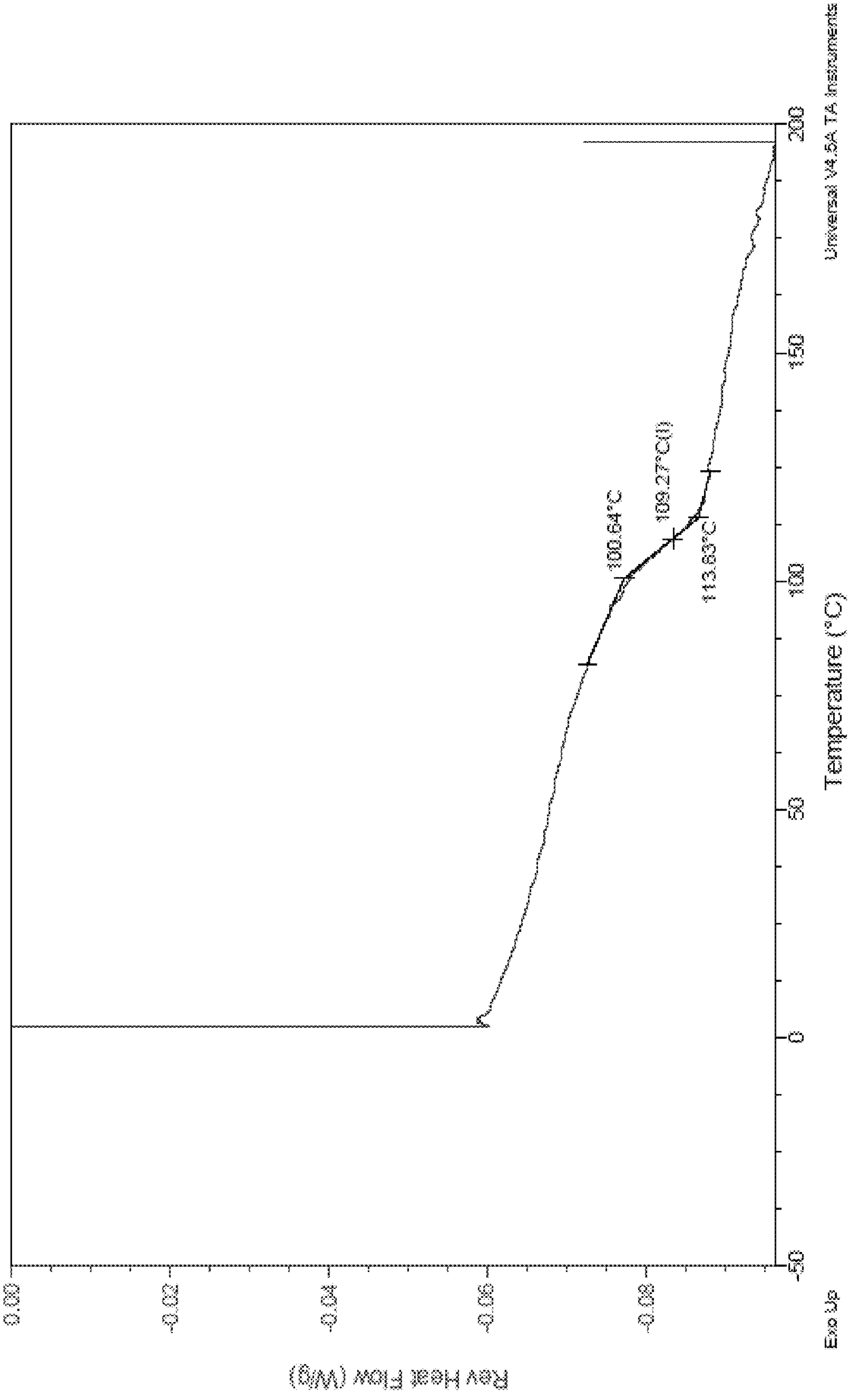
FIG. 2 shows an mDSC thermogram (reversing signal) of the API/HPMC 603 (1:2) SDD showing a Tg at 109° C.

FIG. 2 is an mDSC thermogram (reversing signal) of the API/HPMC 603 (1:2) SDD showing a Tg at 109° C.

Figure 3:
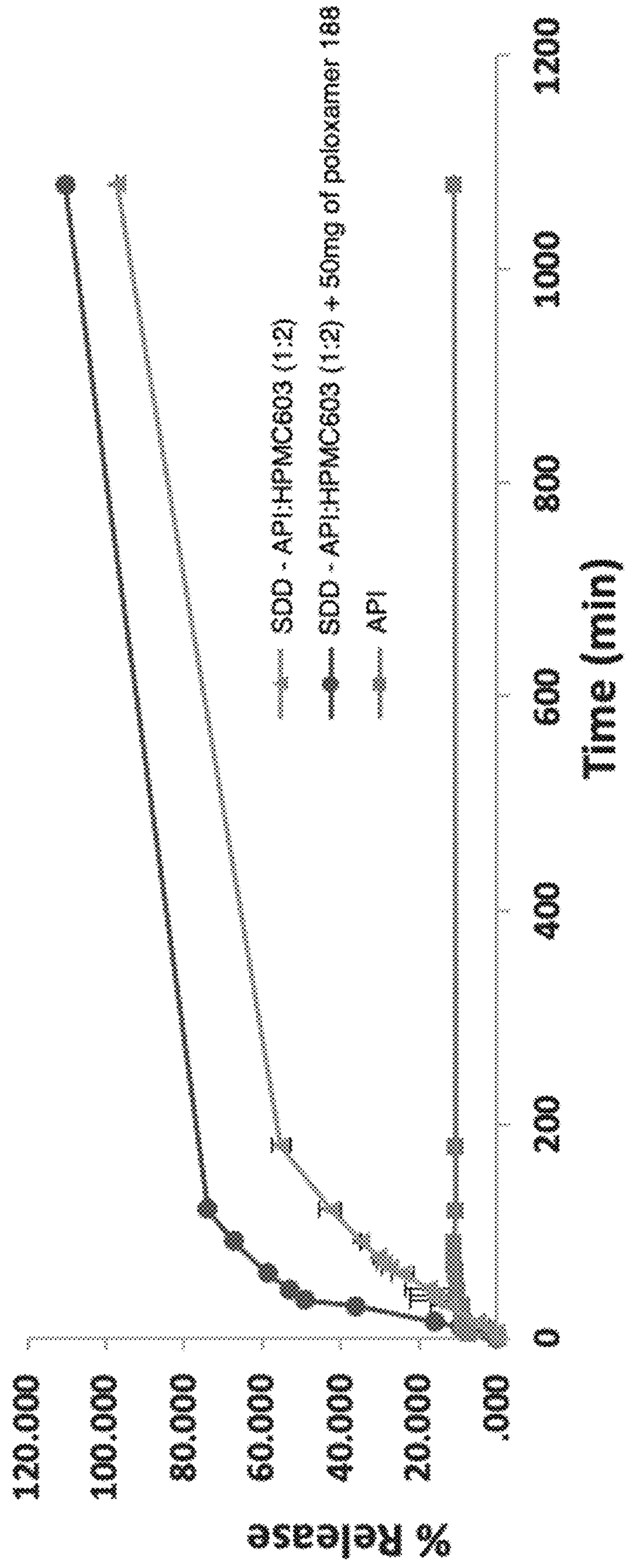
FIG. 3 shows the dissolution results of the API-HPMC 603 SDD compared to non-formulated API.

Dissolution results of the API-HPMC 603 SDD compared to non-formulated API are shown in FIG. 3. Due to the low solubility of API, less than 12% API (i.e. 0.011 mg/mL in FaSSIF) from capsules containing API only was released in the dissolution media over 18 hours. Compared to the non-formulated API, API-HPMC603 SDD filled capsules showed at least 8 times higher solubility of API and a much-improved dissolution profile with over 97% API released (0.096 mg/mL in FaSSIF) within 18 hours.

As plug formation was observed for the SDD, a third formulation composed of a physical mixture of Poloxamer 188 with the SDD was prepared. The addition of poloxamer 188 prevented plug formation and resulted in a faster rate of disintegration/dissolution of API (i.e. 74% with Poloxamer 188 (0.073 mg/mL) vs. 43% without Poloxamer 188 (0.042 mg/mL) after 2 hours of dissolution).

A 4-week stability study was conducted on the prepared SDD's with and without poloxamer. Following storage at 25° C./60% RH and 40° C./75% RH for up to 4 weeks there was no change in assay or dissolution profile. The SDD's remained amorphous at both conditions, however, the Tg appeared to shift to 60-70° C. during storage.

As an alternative to poloxamer 188, the surfactant SLS was also evaluated to aid in the dispersion of the SDD. SDD's with both poloxamer and Sodium Lauryl Sulfate (SLS) yielded similar release profiles, however, in the presence of SLS, the SDD powder was visually dispersed completely in the dissolution medium within 10 minutes, which is faster than with the use of Poloxamer 188 (~30 minutes).

Spray Coating/Drug Layering of Amorphous Compound of Formula I

Drug layering on a small scale (30 g of layered pellets) was conducted by using an Aeromatic coater (fluid bed laboratory unit, STREA-1 from GEA Niro Inc). The composition of the coating solution and the parameters used during the drug layering process are provided below.

Coating Solution and Parameters Used for the Drug Layering Process:

| | | |
|---|---|---|
| Composition of coating solution | Solvent | Acetone/water 80/20 |
| | Concentration of API | 30 mg/mL |
| | Concentration of HPMC603 | 60 mg/mL |
| Inlet Temperature | 50° C. | |
| Outlet Temperature | 40° C. | |
| Nozzle air pressure | 0.9-1 Bar | |
| Air Flow | 50% (110 $m^3$/hr) | |
| Spray Rate | 1.5 mL/min (0.10 g dry material/min) | |
| Drying | 20 minutes at 50° C. (inlet temperature) | |

The coating solution for applying the drug: polymer mixture over the inert cores was prepared as follows. To prepare 200 mL coating solution, 12 g of HPMC 603 was added into 40 mL of distilled water in a beaker and the mixture was heated to 70-80° C., stirring using a magnetic stirrer. After the HPMC 603 was fully dispersed, the solution was cooled down to room temperature resulting in a clear HPMC 603 solution. 140 mL acetone was added into the solution and the mixture was stirred using a magnetic stirrer until a homogenous solution was achieved. To this, 6 g of API was added and the solution was stirred until all of the API dissolved. During the process, the beaker was sealed using parafilm to prevent the evaporation of acetone. Finally, the coating solution was sieved through 0.25 mm mesh prior to use.

30 g VIVAPUR® microcrystalline cellulose (MCC) spheres 700 (710-1000 μm) from JRS was used for drug layering. The final composition of the drug layered MCC spheres is shown below.

Composition of Drug Layered Pellets:

| Material | % w/w |
|---|---|
| VIVAPUR ® MCC 700 spheres | 64 |
| API | 12 |
| HPMC603 | 24 |
| Total | 100 |

The resulting drug layered pellets were analysed by UV-HPLC to determine the drug loading as well as by SEM, XRPD and Dissolution in biorelevant media.

The UV-HPLC results showed that the drug loading of the pellets was 12.19% with no degradation of API observed. XRPD showed that API remained amorphous after drug layering.

Figure 4:
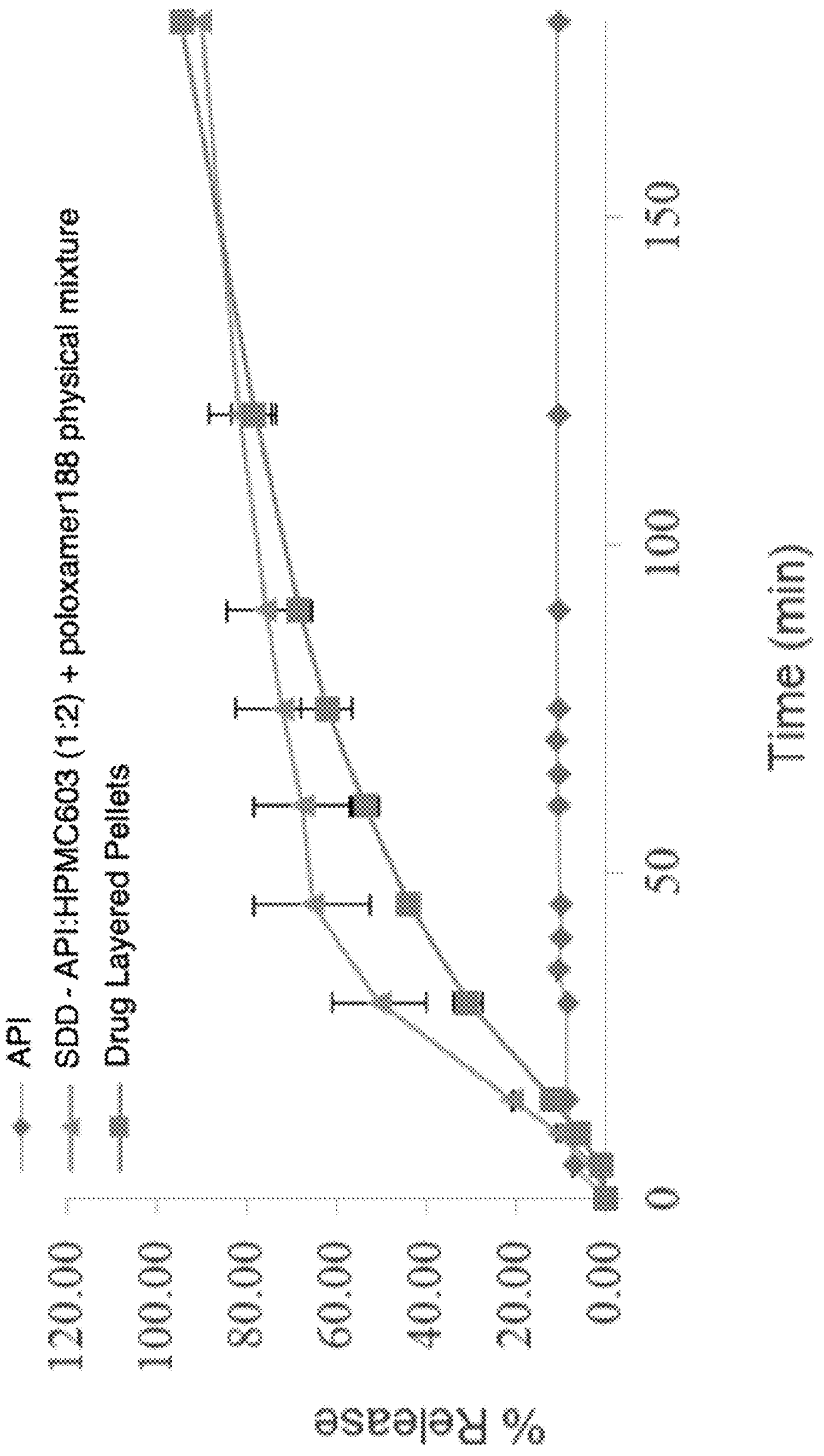
FIG. 4 shows the dissolution profile of the drug-layered pellets compared to the dissolution profiles of the API alone as well an ASD formulation (physical mixture of SDD (API: HPMC603=1:2) and poloxamer 188).

The dissolution profile of the drug-layered pellets was compared to the dissolution profiles of the API alone as well an ASD formulation (physical mixture of SDD (API: HPMC603=1:2) and poloxamer 188) (see FIG. 4). The drug layered pellets show a similar maximum % release to that of the ASD formulation in three hours, whereas the initial release rate was a bit slower with approximately 33% of API released in 30 minutes (as compared to approximately 50% released from the ASD formulation).

To investigate the slower dissolution further, an HPC coating was applied to the surface of the drug layered pellets (7% weight gain). The coating process was conducted using a Caleva mini coater drier and 5 g of drug layered pellets were sprayed for approximately 1 hour with the coating solution to reach a 7% polymer weight gain. The coating solution used was a 5% w/w HPC aqueous solution and the parameters used as well as the composition of the final HPC coated drug layered pellets are shown below.

Parameters Used for HPC Coating:

| | |
|---|---|
| Agitator (Hz) | 11.2 Hz |
| Fan speed (m/s) | 9.2 |
| Inlet air temperature (° C.) | 40 |
| Atomising air pressure (bar) | 0.9 |
| Flow rate | 0.006 g dry material/min |
| Drying | 30 minutes |

Composition of HPC Coated Drug Layered Pellets:

| Material | % w/w |
|---|---|
| MCC 700 spheres | 59.8 |
| API | 11.2 |
| HPMC603 | 22.4 |
| HPC | 6.5 |
| Total | 100 |

Figure 5:
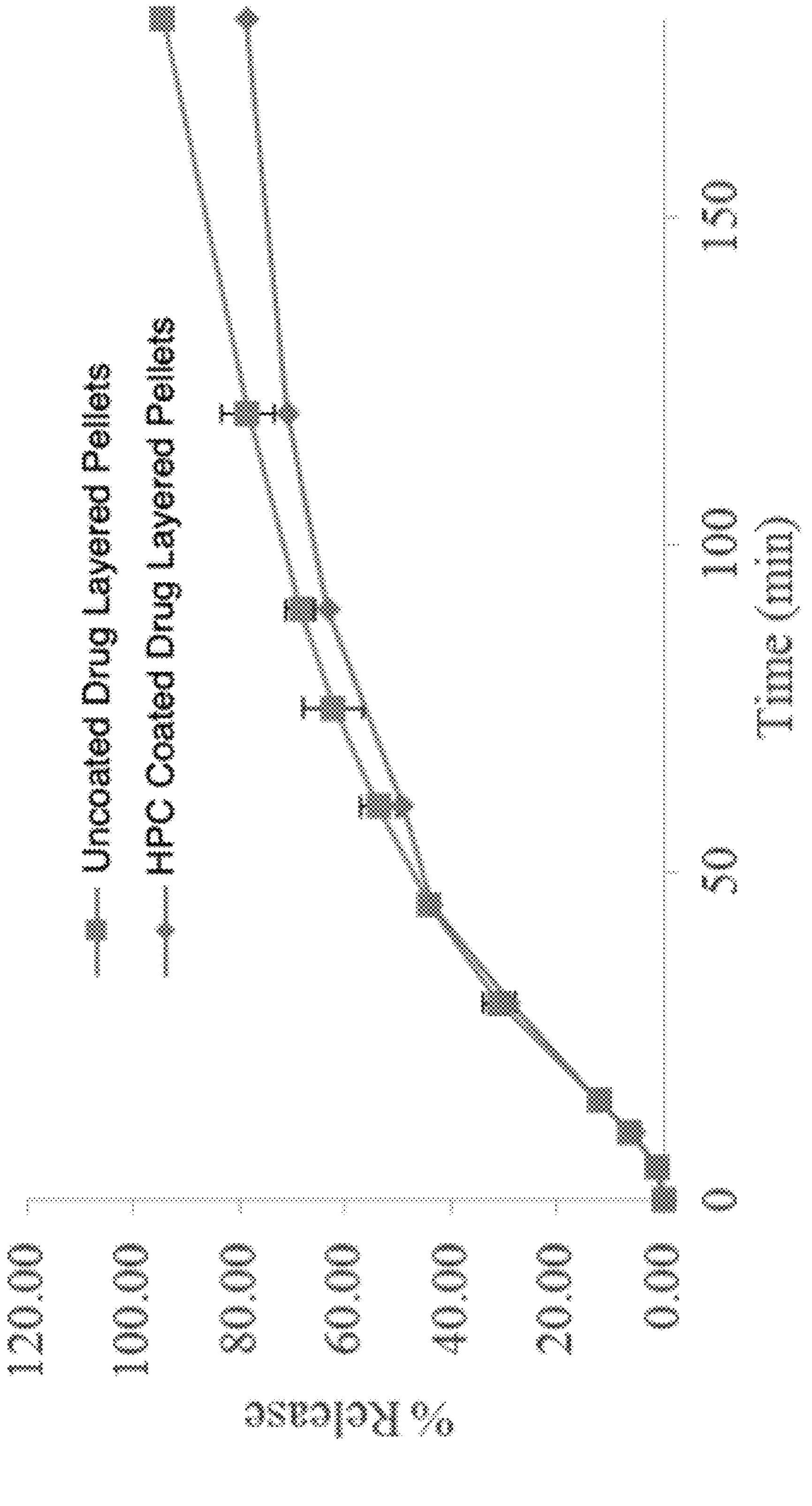
FIG. 5 shows the dissolution profiles of the HPC coated drug-layered pellets and uncoated drug-layered pellets.

The dissolution test of the HPC coated pellets showed that although the HPC coated pellets were fully dispersed in 30 minutes in the biorelevant dissolution media, however the dissolution profile was not improved (see FIG. 5).

A 4-week stability study was conducted on the drug-layered pellets. The drug-layered pellets were manually filled into size-00 Licap hard shell gelatin capsules (410 mg pellets per capsule, equivalent to 50 mg API). The capsules were placed in closed glass vials and were incubated at 25° C./60% RH and 40° C./75%. At each time point (T=0, 7 days and 4 weeks) the samples were analysed/characterized by XRPD, SEM and dissolution.

The results of the stability study show the pellets remain unchanged following storage at 25° C./60% RH and 40° C./75% for 4 weeks. The dissolution profile of the drug layered pellets did not change at either condition. It was also confirmed by XRPD that API remained amorphous with no evidence of recrystallization during the 4-week period when stored at both 25° C./60% RH and 40° C./75%. The SEM results of the drug layered pellets show that no obvious morphology change to the surface of the pellets was observed during the 4-week storage at both 25° C./60% RH and 40° C./75%.

On a larger scale (1-4 kg coated pellets), drug-layering was conducted using a Glatt GPCG3 fluid bed with a 6 or 7-inch Wurster insert. The equipment parameters used during the drug layering process are provided below. Two different drug loadings of MCC spheres were prepared.

Parameters Used for the Drug Layering Process:

| Parameter | Low Dose | High Dose |
|---|---|---|
| Wurster Type | 7 inches | 6 inches |
| Nozzle Diameter | 1.2 mm | 1.2 mm |
| Inlet Temperature | 52-55° C. | 52-55° C. |
| Outlet Temperature | 35-40° C. | 30-35° C. |
| Nozzle air pressure | 1.5 Bar | 1.6 Bar |
| Air Flow | 35 $m^3$/h | 30 $m^3$/h |
| Spray Rate | 12-13 g/min | 8-9 g/min |
| Drying | 30 minutes at 70° C. (inlet temperature) | 30 minutes at 70° C. (inlet temperature) |

The coating solution was prepared as follows. Water was placed in a jacketed mixing bowl and heated to 35-37° C. HPMC was slowly added to the heated water while mixing then the mixture was heated to 52-55° C. and mixing was continued until a homogenous dispersion was formed. The mixture was cooled to room temperature and mixing was continued until a clear solution was obtained. The aqueous HPMC solution and acetone were mixed together in a glass container suitable for feeding solutions to a fluid bed coating machine. The API was dissolved in the aqueous HPMC/acetone mixture. MCC microspheres were transferred to the bowl of a fluid bed coating machine and spray coated with the API/aqueous HPMC/acetone mixture until the desired amount of drug layering was achieved. The final composition of the drug layered MCC spheres is shown below.

Composition of Drug Layered Pellets:

| Material | Low Dose % w/w | High Dose % w/w |
|---|---|---|
| VIVAPUR ® MCC 350 spheres | 96.4 | 64 |
| API | 1.2 | 12 |
| HPMC603 | 2.4 | 24 |
| Total | 100 | 100 |

Use of Pore Forming Agent:

Additional drug layering trials were conducted with the inclusion of pore forming agents in the layering solution. Pore forming agents such as Calcium Dihydrogen Phosphate, Lactose, Hydroxypropyl cellulose and microcrystalline cellulose are excipients added to the layering solution along with HPMC 603 and the compound of formula I which cause the formation of small pores or channels in the coating. The pores allow for more rapid wetting of the layered coating thus increasing the rate of drug release from the coated microspheres. These excipients can be added at up to 20% w/w conc. The excipient can be either dissolved in the aqueous HPMC 603 polymer solution or in the final acetone/water solution containing the compound of formula I before the spray coating.

One example of a drug layered pellet containing a pore forming excipient has the composition below:

Composition of Drug Layered Pellets with a Pore Forming Excipient:

| Material | % w/w |
|---|---|
| VIVAPUR® MCC 350 spheres | 56.8 |
| API | 12 |
| HPMC603 | 24 |
| Calcium dihydrogen Phosphate | 7.2 |
| Total | 100 |

Drug layered pellets were manufactured using the composition above. SEM analysis showed the presence of pores on the surface of the coated pellets. Dissolution testing showed a faster release profile than drug layered pellets without calcium dihydrogen phosphate.

Pharmacokinetic Data in Humans

The first part of this study aims to obtain safety, tolerability and pharmacokinetic data when the compound of formula I is administered orally as a single dose in healthy subjects using the above drug layered formulation.

Experimental Data from Healthy Subject Cohort A1: 5 mg Compound of Formula I (API)

6 healthy subjects received 5 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

Experimental Data from Healthy Subject Cohort A2: 20 mg Compound of Formula I 6 healthy subjects received 20 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24 hours post dose. See tables hereunder.

Experimental Data from Healthy Subject Cohort A3 Fasted: 50 mg Compound of Formula I (API)

6 healthy subjects received 50 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

Experimental Data from Healthy Subject Cohort A3 Fed: 50 mg Compound of Formula I (API)

6 healthy subjects received 50 mg of compound of formula I capsules orally as a single dose in the fed state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

Experimental Data from Healthy Subject Cohort A4: 50 mg Compound of Formula I (API) (as 10×5 mg Capsules)

6 healthy subjects received 50 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

Experimental Data from Healthy Subject Cohort A5: 100 mg Compound of Formula I (API)

6 healthy subjects received 100 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

Experimental Data from Healthy Subject Cohort A6: 200 mg Compound of Formula I (API)

6 healthy subjects received 200 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

Experimental Data from Healthy Subject Cohort A7: 400 mg Compound of Formula I (API)

6 healthy subjects received 400 mg of compound of formula I capsules orally as a single dose in the fasted state, and 2 subjects receive placebo. The first 2 subjects (1 active and 1 placebo) were dosed 24 hours before the remaining subjects. Blood samples for pharmacokinetic analysis of plasma API concentrations were obtained by venipuncture before dosing, and then at 0.5, 1, 1.5, 2, 3, 4, 6, 8, 12, 16, 24, 36, and 48 hours post dose. See tables hereunder.

TABLE 1

Geometric mean (% CV) PK parameters of GB1211 following single oral dose administration

| Parameter (Units) | 5 mg (fasted state) | 20 mg (fasted state) | 50 mg (1 × 50 mg) (fasted state) | 50 mg (10 × 5 mg) (fasted state) |
|---|---|---|---|---|
| $AUC_{0-24}$ (ng · h/mL) | 585 (20.8) | 2670 (11.4) | 3400 (47.7) | 5770 (39.4) |
| $AUC_{0-tlast}$ (ng · h/mL) | 677 (23.4) | 3150 (10.0) | 4180 (45.1) | 6890 (41.1) |
| $AUC_{0-\infty}$ (ng · h/mL) | 712 (24.5) | 3350 (10.0) | 4520 (43.3) | 7480 (42.7) |
| $C_{max}$ (ng/mL) | 75.2 (23.7) | 365 (25.3) | 358 (54.6) | 861 (48.4) |
| $T_{max}{}^{a}$ (h) | 2.00 (1.00-3.00) | 1.75 (1.50-2.00) | 3.00 (2.00-4.00) | 1.75 (1.00-4.00) |
| $t_{1/2}$ (h) | 11.2 (14.9) | 12.4 (12.5) | 12.6 (19.6) | 13.8 (9.8) |
| $T_{lag}{}^{a}$ (h) | 0.00 (0.00-0.00) | 0.00 (0.00-0.50) | 0.00 (0.00-0.50) | 0.00 (0.00-0.00) |

| Parameter (Units) | 50 mg (1 × 50 mg) (fed state) | 100 mg (fasted state) | 200 mg (fasted state) | 400 mg (fasted state) |
|---|---|---|---|---|
| $AUC_{0-24}$ (ng · h/mL) | 3820 (28.1) | 4900 (18.1) | 9050 (40.3) | 15100 (32.3) |
| $AUC_{0-tlast}$ (ng · h/mL) | 4930 (23.4) | 5900 (18.8) | 9050 (40.3) | 19000 (29.3) |
| $AUC_{0-\infty}$ (ng · h/mL) | 5420 (21.3) | 6360 (21.3) | 13100 (49.3) | 21500 (25.1) |
| $C_{max}$ (ng/mL) | 389 (37.9) | 525 (23.6) | 1010 (54.1) | 1550 (36.2) |
| $T_{max}{}^{a}$ (h) | 5.00 (4.00-6.00) | 3.50 (1.50-4.00) | 3.50 (3.00-4.00) | 4.00 (3.00-4.00) |
| $t_{1/2}$ (h) | 12.8 (18.4) | 12.1 (22.3) | 15.1 (49.0) | 14.5 (22.9) |
| $T_{lag}{}^{a}$ (h) | 0.75 (0.50-2.00) | 0.00 (0.00-0.00) | 0.00 (0.00-0.00) | 0.00 (0.00-0.00) |

[a]Median (min – max) presented

The second part of this study aims to obtain safety, tolerability and pharmacokinetic data when the compound of formula I is administered orally dosed twice a day for 10 days in healthy subjects using the above drug layered formulation.

Experimental Data from Healthy Subject Cohort B1: 50 mg Compound of Formula I (API)

8 healthy subjects received 50 mg of compound of formula I capsules and 3 subjects receive placebo orally twice a day for 10 days. Blood samples for pharmacokinetic analysis of plasma API concentrations were obtained by venipuncture before dosing on day 1, and then at 0.5, 1, 1.5, 2, 3, 4, 6, 8, 12, 16, 24, 36, and 48 hours post dose. Blood sampling was repeated on day 10. See tables hereunder.

Experimental Data from Healthy Subject Cohort B2: 100 mg Compound of Formula I 8 healthy subjects received 100 mg of compound of formula I capsules and 3 subjects receive placebo orally twice a day for 10 days. Blood samples for pharmacokinetic analysis of plasma API concentrations were obtained by venipuncture before dosing on day 1, and then at 0.5, 1, 1.5, 2, 3, 4, 6, 8, 12, 16, 24 hours post dose. Blood sampling was repeated at day 10. See tables hereunder.

TABLE 2

Geometric mean (% CV) PK parameters of GB1211 following multiple oral dose administration

| Parameter (Units) | 50 mg BID (fasted state) Day 1 | 50 mg BID (fasted state) Day 10 | 100 mg BID (fasted state) Day 1 | 100 mg BID (fasted state) Day 10 |
|---|---|---|---|---|
| $AUC_{0-12}$ (ng · h/mL) | 2220 (23.3) | 5130 (29.0) | 3570 (42.8) | 7530 (21.1) |
| $AUC_{0-\infty}$ (ng · h/mL) | $3390^{b}$ (22.1) | NA | $5280^{b}$ (42.5) | NA |
| $AUC_{\%-extrap}$ (%) | $34.0^{b}$ (15.7) | NA | $32.1^{b}$ (13.1) | NA |
| $C_{max}$ (ng/mL) | 330 (31.8) | 658 (35.4) | 546 (53.5) | 975 (21.9) |
| $C_{min}$ (ng/mL) | NA | 249 (26.2) | NA | 338 (27.5) |
| $T_{max}{}^{a}$ (h) | 4.00 (1.50-4.00) | 2.50 (1.50-4.00) | 3.00 (2.00-4.00) | 3.00 (2.00-4.00) |
| $t_{1/2}$ (h) | $7.34^{b}$ (11.3) | 20.2 (32.9) | $7.04^{b}$ (9.0) | 12.5 (17.4) |
| $RA_{AUC}$ | NA | 2.31 (32.9) | NA | 2.11 (31.4) |

[a]Median (min – max) presented

NA = Not Applicable

[b]$t_{1/2}$ and derived parameters are unreliable due to short sampling duration of 0-12 hours; reported only for exploratory purposes in this interim report

We claim:

1. A pharmaceutical composition comprising:

an amorphous form of a compound of formula I (I)

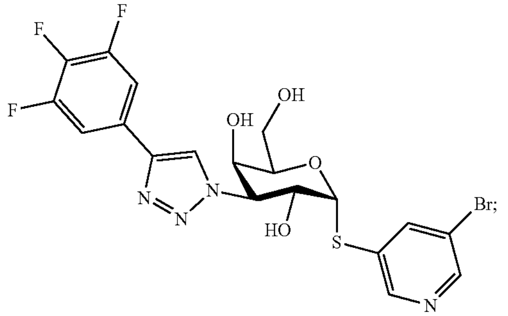

a polymer for stabilizing the amorphous form of the compound of formula I, wherein the polymer comprises hydroxy propyl methyl cellulose (Hypromellose);

and optionally a pharmaceutically acceptable additive;

wherein a weight ratio of the amorphous compound of formula I to the polymer is in a range from 1:2 to 1:5.

2. The pharmaceutical composition of claim 1, comprising the amorphous compound of formula I in an amount of 0.1 mg to 1000 mg.

3. An amorphous solid dispersion composition comprising:

a mixture of an amorphous compound of formula I:

(I)

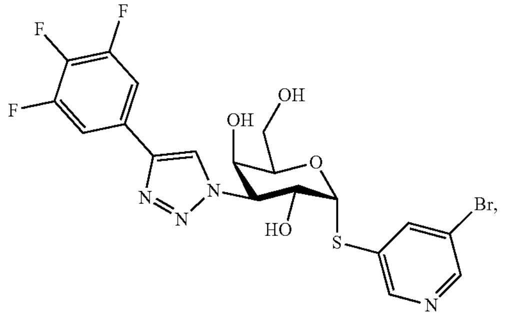

and a polymer for stabilizing the amorphous form of the compound of formula I, and optionally a pharmaceutically acceptable additive;

wherein a weight ratio of the amorphous compound of formula I to the polymer is in a range from 1:2 to 1:5;

wherein the polymer for stabilizing the amorphous form of the compound of formula I comprises hydroxy propyl methyl cellulose (Hypromellose).

4. The amorphous solid dispersion composition of claim 3, wherein the mixture comprises the weight ratio of the amorphous compound of formula I to the polymer in the range from 1:2 to 1:3.

5. The amorphous solid dispersion composition of claim 3, wherein the polymer is present in a concentration of at least 0.1% w/w, and optionally a pharmaceutically acceptable additive adding up to 100% w/w.

6. The amorphous solid dispersion composition of claim 3, comprising the amorphous compound of formula I in an amount of 0.1 mg to 1000 mg.

7. A tablet composition for oral administration comprising the amorphous solid dispersion composition of claim 3.

8. A drug layered composition comprising a) an inert solid core having an outer surface and b) a mixture of amorphous compound of formula I:

(I)

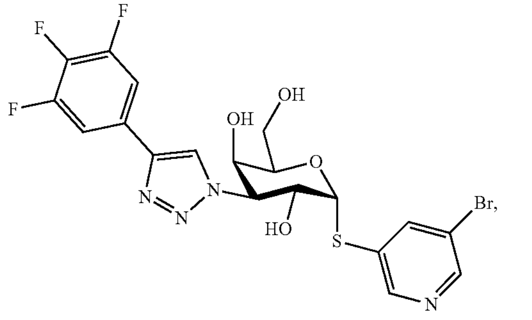

a polymer for stabilizing the amorphous form of the compound of formula I and optionally a pharmaceutically acceptable additive; wherein the mixture is a layer on the outer surface of the inert solid core;

wherein a weight ratio of the amorphous compound of formula I to the polymer is in a range from 1:2 to 1:5;

wherein the polymer for stabilizing the amorphous form of the compound of formula I comprises hydroxy propyl methyl cellulose (Hypromellose).

9. The drug layered composition of claim 8, wherein the mixture dissolved in a suitable solvent is sprayed onto the surface of the inert solid core.

10. The drug layered composition of claim 8, wherein the mixture comprises the weight ratio of the amorphous compound of formula I to the polymer in the range from 1:2 to 1:3.

11. The drug layered composition of claim 8, wherein the polymer is present in a concentration from 1% w/w to 40% w/w, the inert solid core is present in a concentration of 40% w/w to 98.5% w/w, and optionally a pharmaceutically acceptable additive adding up to 100% w/w.

12. A capsule composition for oral administration comprising the drug layered composition of claim 8.

13. The drug layered composition of claim 8, wherein the pharmaceutically acceptable additive is present and comprises a pore forming excipient.

14. The drug layered composition of claim 13, wherein the pore forming excipient is present in a concentration up to 20% w/w in the layer.

15. The drug layered composition of claim 13, wherein the pore forming excipient is selected from the group consisting of Calcium Dihydrogen Phosphate, Lactose, Hydroxypropyl cellulose and microcrystalline cellulose.

16. The drug layered composition of claim 8, wherein the inert solid core is made of a material selected from the group consisting of sugars, and microcrystalline cellulose (MCC).

17. The drug layered composition of claim 8, wherein the inert solid core has a size in the range from 50 to 2000 μm.

18. The drug layered composition of claim 8, comprising the amorphous compound of formula I in an amount of 0.1 mg to 1000 mg.

19. A method for treatment of a disease or disorder selected from the group consisting of inflammation; fibrosis, comprising pulmonary fibrosis, liver fibrosis, kidney fibrosis, ophthalmological fibrosis and fibrosis of the skin and heart; scarring; keloid formation; aberrant scar formation; surgical adhesions; septic shock; cancer, comprising carcinomas, sarcomas, leukemias and lymphomas, wherein lymphomas comprises T-cell lymphomas; metastasising cancers; autoimmune diseases, comprising psoriasis, rheumatoid arthritis, Crohn's disease, ulcerative colitis, ankylosing spondylitis, and systemic lupus erythematosus; metabolic disorders; heart disease; heart failure; pathological angiogenesis, comprising ocular angiogenesis or a disease or condition associated with ocular angiogenesis and neovascularization related to cancer; and eye diseases, comprising age-related macular degeneration and corneal neovascularization; atherosclerosis; metabolic diseases comprising type 2 diabetes, insulin resistens, and obesity; Diastolic HF; asthma and other interstitial lung diseases, including Hermansky-Pudlak syndrome, and mesothelioma; liver disorders, comprising non-alcoholic steatohepatitis or non-alcoholic fatty liver disease, in a mammal, comprising administering a therapeutically effective amount of the amorphous solid dispersion composition of claim 3.

20. The method of claim 19, wherein the composition comprising the compound of formula I is administered once daily or twice daily.

21. A method for treatment of a disease or disorder selected from the group consisting of inflammation; fibrosis, comprising pulmonary fibrosis, liver fibrosis, kidney fibrosis, ophthalmological fibrosis and fibrosis of the skin and heart; scarring; keloid formation; aberrant scar formation; surgical adhesions; septic shock; cancer, comprising carcinomas, sarcomas, leukemias and lymphomas wherein lymphomas comprises T-cell lymphomas; metastasising cancers; autoimmune diseases, comprising psoriasis, rheumatoid arthritis, Crohn's disease, ulcerative colitis, ankylosing spondylitis, and systemic lupus erythematosus; metabolic disorders; heart disease; heart failure; pathological angiogenesis, comprising ocular angiogenesis or a disease or condition associated with ocular angiogenesis, and neovascularization related to cancer; and eye diseases, comprising age-related macular degeneration and corneal neovascularization; atherosclerosis; metabolic diseases comprising type 2 diabetes, insulin resistance, and obesity; Diastolic HF; asthma and other interstitial lung diseases, including Hermansky-Pudlak syndrome, and mesothelioma; liver disorders, comprising non-alcoholic steatohepatitis or non-alcoholic fatty liver disease, in a mammal, comprising administering a therapeutically effective amount of the drug layered composition of claim 8.

22. The method of claim 21, wherein the composition comprising the compound of formula I is administered once daily or twice daily.

23. The pharmaceutical composition of claim 1, wherein the polymer for stabilizing the amorphous form of the compound of formula I further comprises at least one selected from the group consisting of polyethylene glycol (PEG), carboxymethylethylcellulose (CMEC), ethyl cellulose, hydroxyethylcellulose (HEC), methyl cellulose (MC), polyvinylpyrrolidone vinyl acetate (PVP/VA), Polyvinylpyrrolidone, Hypromellose phthalate, Hypromellose acetate succinate, methacrylic acid-ethyl acrylate copolymer, and Lauroyl polyoxyl-32 glyceride.

24. The amorphous solid dispersion composition of claim 3, wherein the polymer for stabilizing the amorphous form of the compound of formula I further comprises at least one selected from the group consisting of polyethylene glycol (PEG), carboxymethylethylcellulose (CMEC), ethyl cellulose, hydroxyethylcellulose (HEC), methyl cellulose (MC), polyvinylpyrrolidone vinyl acetate (PVP/VA), Polyvinylpyrrolidone, Hypromellose phthalate, Hypromellose acetate succinate, methacrylic acid-ethyl acrylate copolymer, and Lauroyl polyoxyl-32 glyceride.

25. The drug layered composition of claim 8, wherein the polymer for stabilizing the amorphous form of the compound of formula I further comprises at least one selected from the group consisting of polyethylene glycol (PEG), carboxymethylethylcellulose (CMEC), ethyl cellulose, hydroxyethylcellulose (HEC), methyl cellulose (MC), polyvinylpyrrolidone vinyl acetate (PVP/VA), Polyvinylpyrrolidone, Hypromellose phthalate, Hypromellose acetate succinate, methacrylic acid-ethyl acrylate copolymer, and Lauroyl polyoxyl-32 glyceride.

* * * * *